United States Patent
Knudsen

(10) Patent No.: US 7,047,967 B2
(45) Date of Patent: May 23, 2006

(54) INHALER

(75) Inventor: Lars Knudsen, Struer (DK)

(73) Assignee: AstraZeneca AB, Sodertalje (SE)

( * ) Notice: Subject to any disclaimer, the term of this patent is extended or adjusted under 35 U.S.C. 154(b) by 171 days.

(21) Appl. No.: 10/221,708

(22) PCT Filed: Mar. 16, 2001

(86) PCT No.: PCT/SE01/00560

§ 371 (c)(1),
(2), (4) Date: Dec. 3, 2002

(87) PCT Pub. No.: WO01/70316

PCT Pub. Date: Sep. 27, 2001

(65) Prior Publication Data

US 2003/0183225 A1  Oct. 2, 2003

(30) Foreign Application Priority Data

Mar. 18, 2000 (GB) .................. 0006528.4

(51) Int. Cl.
*A61M 16/00* (2006.01)
*A62B 27/00* (2006.01)
*A62B 9/00* (2006.01)
*G08B 3/00* (2006.01)
*G08B 5/00* (2006.01)

(52) U.S. Cl. .................. 128/202.22; 128/200.14; 128/200.23; 128/202.27; 128/205.23

(58) Field of Classification Search ......... 128/200.14, 128/200.23, 202.22, 202.27, 204.21, 203.12, 128/204.23, 205.23; 239/338; 222/325, 222/30, 23, 14, 153.01; 116/200

See application file for complete search history.

(56) References Cited

U.S. PATENT DOCUMENTS

| 4,817,822 | A | * | 4/1989 | Rand et al. ................... 222/38 |
| 5,507,277 | A | * | 4/1996 | Rubsamen et al. ..... 128/200.14 |
| 5,520,166 | A | * | 5/1996 | Ritson et al. .......... 128/200.14 |
| 5,549,101 | A | * | 8/1996 | Trofast et al. ......... 128/203.15 |
| 5,718,355 | A | * | 2/1998 | Garby et al. .................. 222/36 |
| 5,755,218 | A | * | 5/1998 | Johansson et al. ..... 128/200.14 |
| 5,799,651 | A | * | 9/1998 | Garby et al. .......... 128/200.23 |
| 5,809,997 | A | * | 9/1998 | Wolf ..................... 128/200.23 |
| 5,813,397 | A | * | 9/1998 | Goodman et al. ..... 128/200.14 |
| 6,148,815 | A | * | 11/2000 | Wolf ..................... 128/205.23 |
| 6,435,372 | B1 | * | 8/2002 | Blacker et al. ................ 222/23 |
| 6,729,330 | B1 | * | 5/2004 | Scarrott et al. ........ 128/205.23 |

FOREIGN PATENT DOCUMENTS

| GB | 2 262 452 A | 6/1993 |
| GB | 2 263 068 A | 7/1993 |
| WO | WO 99/49916 | 10/1999 |
| WO | WO 00/16835 | 3/2000 |
| WO | WO 00/16838 | 3/2000 |

* cited by examiner

*Primary Examiner*—Henry Bennett
*Assistant Examiner*—Amanda Wieker
(74) *Attorney, Agent, or Firm*—Fish & Richardson P.C.

(57) ABSTRACT

An inhaler for holding a canister (2) of medicament. The canister (2) has a mount (26) secured thereto mounting an indication member (41) movable slidably from a first state to a second state. A ratchet arrangement (41a, 42) is provided between the mount (26) and the indication member (41) to make the movement irreversible. The inhaler has a catch (49) for moving the indication member from the first state to the second state on removal of the canister (2) from the inhaler. An electrical switch contact (48) detects the state of the indication member (41), thereby providing an indication of whether the canister (2) has been used before. An LCD display is controlled in response to the detection.

27 Claims, 15 Drawing Sheets

INHALER

CROSS REFERENCE TO RELATED APPLICATIONS

The present application is a national phase application under 35 U.S.C. Section 371 filed from International Patent Application PCT/SE01/00560 filed 16 Mar. 2001, which claims priority to United Kingdom patent application Serial. No. 0006528.4, filed 18 Mar. 2000. The contents of these applications are incorporated herein by reference in their entirety.

BACKGROUND OF THE INVENTION

The present application relates to an inhaler for delivery of medicament from a canister.

Inhalers are commonly used to deliver a wide range of medicaments. The inhaler holds a canister of medicament which is actuatable, for example by compression to deliver a dose of medicament. Some known inhalers are provided with an actuation mechanism for actuating the canister, which may be breath-actuated, ie. arranged to actuate the canister in response to inhalation at a mouthpiece in the inhaler.

Desirably, the inhaler is reusable with different canisters. If the canister is reusable there is a risk of mounting a canister which has already been partly or completely used. This can result in the canister expiring unexpectedly. For example, if the inhaler includes a dose counter, this will give an incorrect measure of the doses remaining if a full canister is assumed when a used canister is inserted. This problem is at best annoying to the user and at worst dangerous if a dose of medicament is needed urgently.

SUMMARY OF THE INVENTION

According to a first aspect of the present invention, there is provided an inhaler for holding a canister of medicament, in combination with the canister, the canister having a mount secured thereto mounting an indication member movable irreversibly from a first state to a second state;

the inhaler having means for moving the indication member from the first state to the second state on removal of the canister from the inhaler and detection means for detecting the state of the indication member.

Thus, fresh canisters may be supplied with the indication member in the first state and they will be mounted to the inhaler in this state. Subsequently when the canister is removed from the inhaler, the indication member is moved from the first state to the second state. As this is irreversible, the indication member will remain in the second state even if the canister is mounted in the inhaler once again. As the detection means detects the state of the indication member, this detection provides an indication of whether the canister is a fresh canister or has been used before. Various action may be taken in response to this detection. For example, the inhaler may have display means for displaying an indication of the state of the indication member when a canister is held by the inhaler. If a dose counter is provided, this could be disabled when a canister is inserted with the indication member in the second state. It would even be conceivable to disable an actuation mechanism provided to actuate the canister.

Numerous different structures for the indication member are possible, but it is preferred that the indication member is slidably mounted to the mount because this provides a simple but reliable structure.

Preferably, a ratchet arrangement is provided between the mount and the indication member, which is preferred for reasons of simplicity and reliability.

A preferred form of detection means is an electrical switch contact.

Advantageously, the indication member is shaped to engage the detection means only when the canister is held by the inhaler with the indication member in its first state. This arrangement has the advantage of being fail-safe. That is, if the indication member becomes broken or removed, so that it is not possible to detect whether or not the canister has been used before, then the detection means will not be engaged. Consequently, the inhaler will assume that the canister has been used before which is safer than assuming a fresh canister.

According to a second aspect of the present invention, there is provided an inhaler for replacably holding a canister of medicament and having detection means for detecting whether a canister is held by the inhaler.

The inhaler having detection means has numerous advantages. The operation of the inhaler may be controlled depending on whether or not a canister is detected. For example, if a display means is provided this can display an indication of whether or not a canister is held by the inhaler thereby allowing the user to easily determine whether a canister is loaded. If an actuation mechanism is provided, operation of the actuation mechanism could be inhibited until a canister is detected.

Preferably, the detection means is arranged to detect an indication means provided on a mount secured to the canister. Provision of a mount with the indication member formed thereon is particularly advantageous because it allows a detection means to be more easily designed and constructed, as compared to if the detection means had to detect the canister itself. This in turn improves reliability. For example it becomes easy to design the detection means as an electrical switch contact.

The canister and inhaler may be separately provided, so independent protection is sought for each element, as well as the combination.

Both aspects of the present invention are embodied in the inhaler described below by the same structural elements, so the features of the two aspects may be freely combined and interchanged.

DESCRIPTION OF DRAWINGS

To allow better understanding, the inhaler which embodies the present invention will now be described by way of non-limitative example with reference to the accompanying drawings, in which.

DETAILED DESCRIPTION

Figure 1:
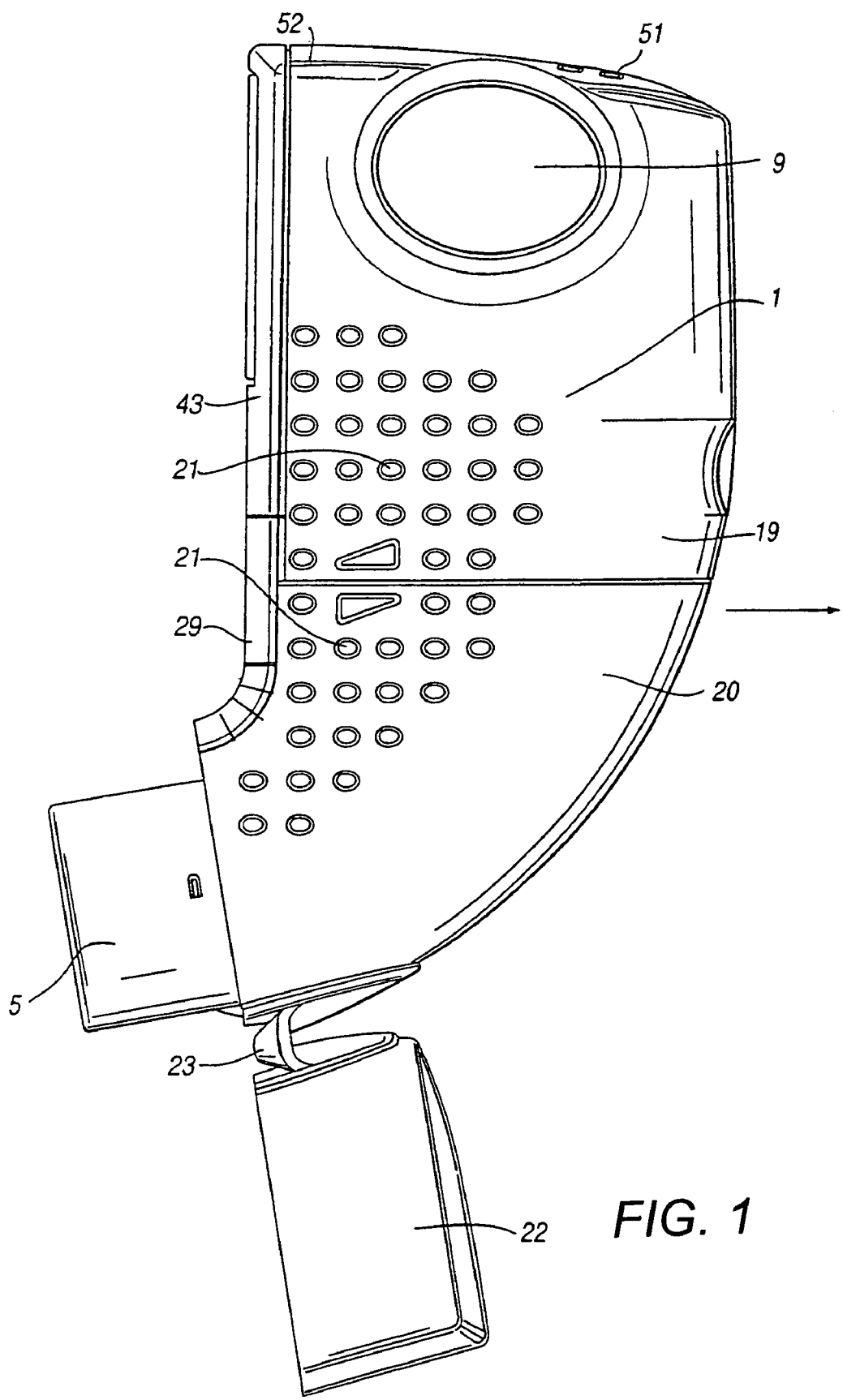
FIG. 1 is a side view of the inhaler.

As illustrated in FIG. 1, the inhaler has a housing 1 comprising an upper portion 19 and a lower portion 20. As illustrated in the cross-sectional view of FIG. 2, the upper housing portion 19 is a hollow shell which holds a canister 2 of medicament having a generally cylindrical body 3 held with its axis in a predetermined direction, vertical in FIG. 2. The upper housing portion 19 houses an actuation mechanism for actuating the canister 2 which will be described in more detail below.

The interior of the upper housing portion 19 is open to the atmosphere by means of air inlets 51 formed in the upper wall 52 of the upper housing portion 19. The location of the air inlets 51 minimises occlusion by the users hand which will normally grip the sides of the housing 1 and not cover the upper wall 52.

The canister 2 is compressible to deliver a dose of medicament. In particular the canister 2 has a valve stem 4 which is compressible relative to the body 3 to deliver a dose of medicament from the valve stem 4. The canister is of a known type including a metering chamber which captures a defined volume the medicament from the body 3 of the canister 2. This volume of medicament is delivered as a metered dose from the valve stem 4 on compression of the valve stem 4 relative to the body 3. The valve stem 4 is weakly biassed outwardly by an internal valve spring (not shown) to reset the canister 2 after compression for refilling the metering chamber.

The lower housing portion 20 is a hollow shell connected to the upper housing portion 19 by a sliding joint (not shown) which allows the lower portion 20 to be separated in the direction of the arrow in FIG. 1 by the user gripping textured surfaces 21 formed on the upper and lower housing portions 19 and 20. A cap 22 is hinged to the lower housing portion 20 by a flexible joint 23 to cover and uncover a mouthpiece 5 protruding from the lower housing portion 20.

Figure 2:
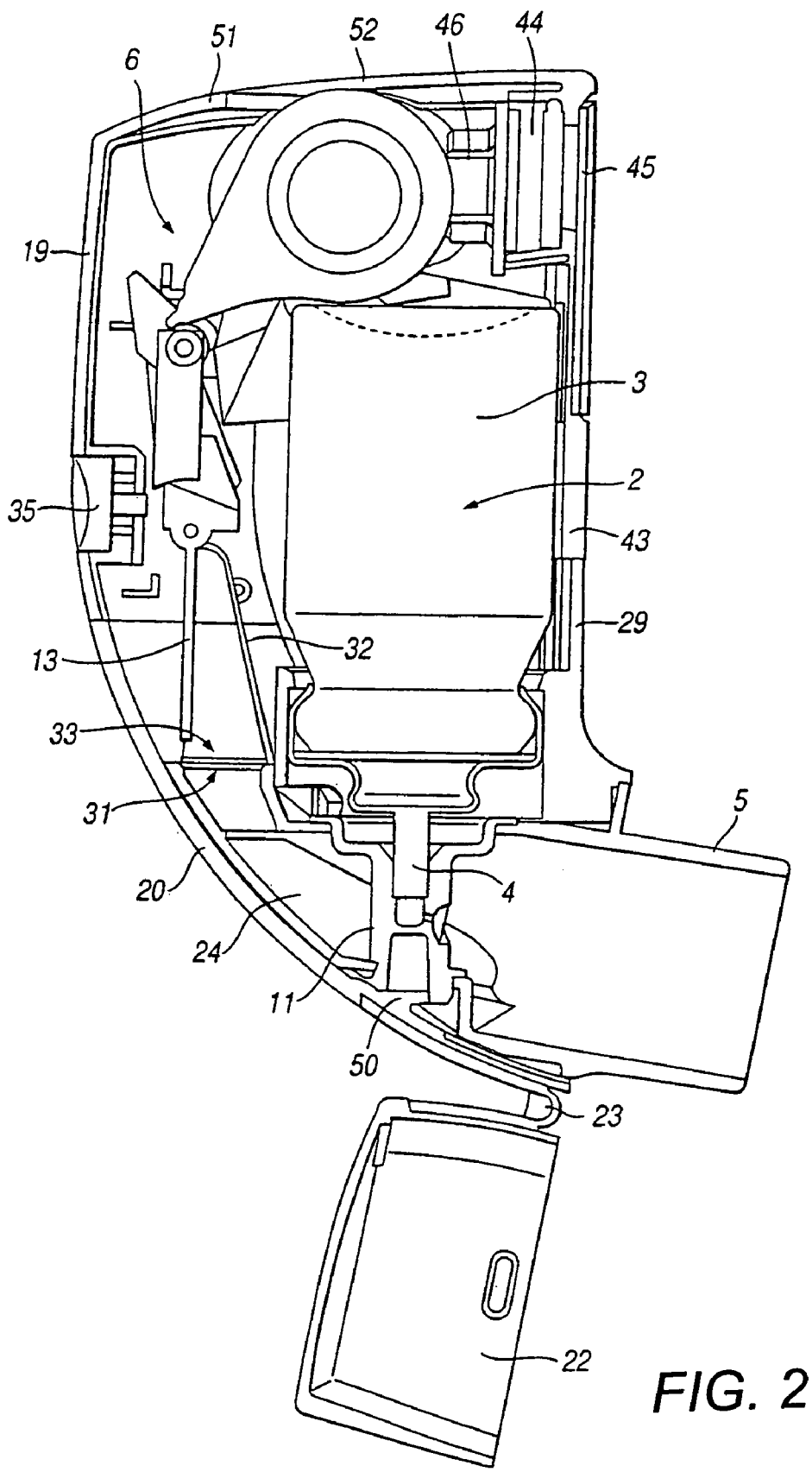
FIG. 2 is a cross-sectional view of the inhaler illustrating the housing and duct.
Figure 3:
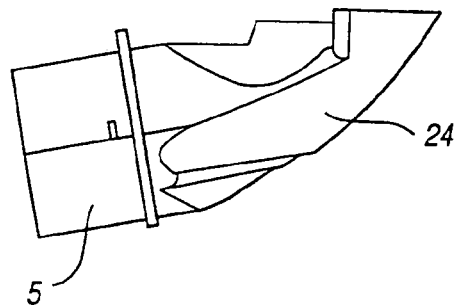
FIG. 3 is a side view of the duct.

As shown in FIG. 2, the lower housing portion 20 houses a duct 24 which is integrally formed with the mouthpiece 5, as illustrated in isolation in FIG. 3.

Figure 4:
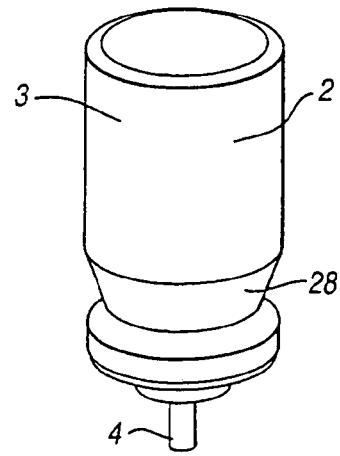
FIG. 4 is a side view of the canister and duct assembled together.
Figure 4:
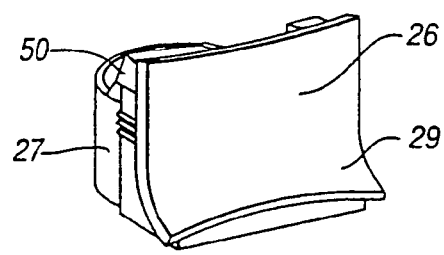
Figure 4:
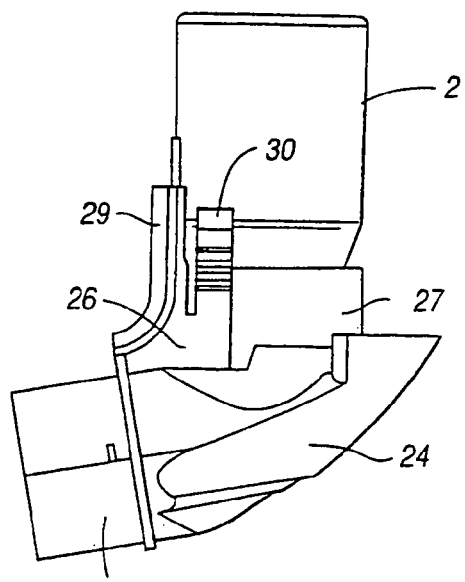
Figure 5:
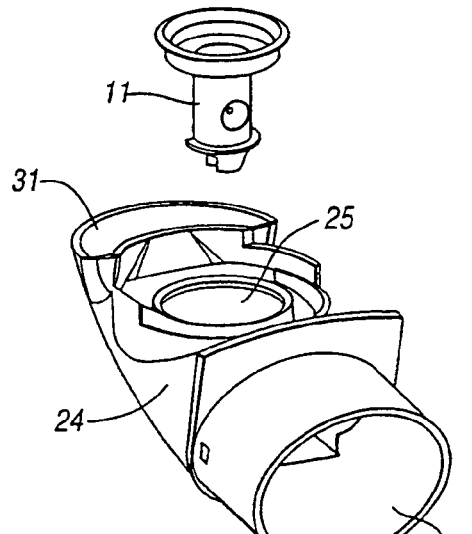
FIG. 5 is an exploded view of the canister, collar and duct.
Figure 6:
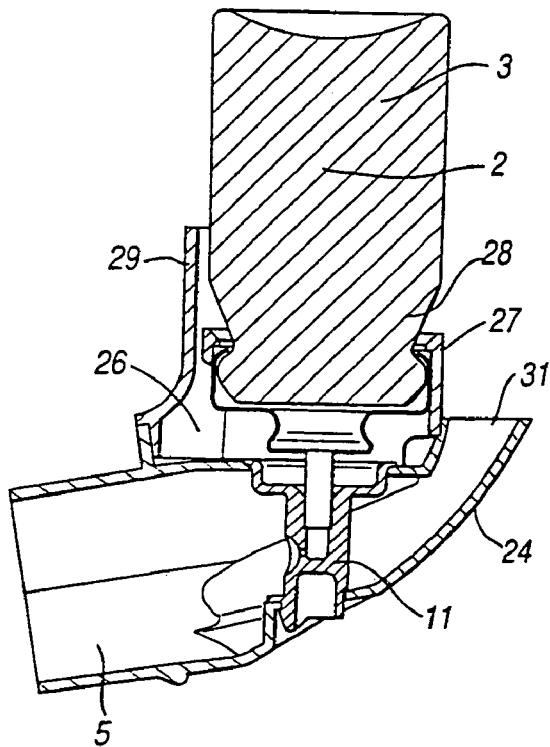
FIG. 6 is a cross-sectional view of the canister and dust assembled together.

The duct 24 is assembled with a canister 2 as shown in FIGS. 4 to 6. The duct 24 receives a nozzle block 11 in an opening 25. The valve stem 4 of the canister is received in the nozzle block 11 which is arranged to direct a dose of medicament delivered from the valve stem 4 out of the inhaler through the mouthpiece 5. The duct 24 and nozzle block 11 are separately formed. This allows each to be manufactured and subsequently assembled. This produces manufacturing and logistical savings because it facilitates different nozzle block designs being incorporated with a single duct design and vice versa.

A collar 26 is permanently connected to the canister 2. The collar 26 includes an annular retaining ring 27 permanently fitted around a necked portion 28 of the canister body 3. The retaining portion 27 prevents removal of the collar 26 from the canister such that the collar 26 is removed and replaced together with the canister 2. However, the retaining portion 27 and the canister 2 have a small degree of relative movement along the axis of the canister 5 to allow compression of the canister body 2 towards the valve stem 4.

The collar 26 further includes a front panel 29 integrally formed with the retaining ring 27. When the canister 2 is inserted in the housing 1, the front panel 29 of the collar 26 closes an opening formed between the upper housing portion 19 and the lower portion 20 and therefore forms a part of the outer wall of the housing 1. Accordingly, the presence or absence of the front panel 29 provides a visual indication to the user of whether or not a canister 2 has been inserted in the canister, because the collar 26 is permanently connected to the canister 2.

A pair of catch arms 30 integrally formed with the front panel 29 of the sides of the collar 26 catch the interior surface of the upper housing portion 19 to hold the collar 26 and the canister 2 in the upper housing portion 19.

The lower housing portion 20 has a stud 50 which locates the end of the nozzle block 11 as shown in FIG. 2 to hold the lower housing portion 20 and the duct 24 in place relative to one another. However, the lower housing portion 20 is not retained on the duct 24, so may be removed from the upper housing portion 19 leaving the canister 2 inserted in the upper housing portion 19 and the duct 24 held on the canister 2 by the valve stem 4 being inserted in the nozzle block 11. The duct 24 and nozzle block 11 may subsequently be slid off the valve stem 4 for cleaning or replacement. The canister 2 and collar 26 may be slid out from the upper housing portion 19 after depression of the catch arms 30. Subsequently a replacement canister 2 and collar 26 may be inserted.

Typically a new duct 24 and nozzle block 11 will be provided to the user with each new canister 2 so that the duct 24 and mouthpiece 5 are regularly replaced to prevent damage or dirt building up over time. The duct 24 has an opening 31 at its end opposite from the mouthpiece 5.

As shown in FIG. 2, the upper housing portion 19 holds a flap duct 32 which extends from a flow inlet 33 to a flap 13 which forms part of the triggering mechanism for the actuation mechanism as described in detail below. Therefore the duct 24 housed in the lower housing portion 19 and the flap duct 32 together define a composite duct shaped to direct the inhalation flow from the mouthpiece 5 to the flap 13. The composite duct formed by the duct 24 and the flap duct 32 is shaped to control the flow to the flap 13 to provide appropriate flow characteristics for proper operation of the flap 13.

The inhaler is further provided with an actuation mechanism 6. To assist understanding, a general description of the overall structure and operation of the actuation mechanism 6 will first be given.

An actuation force for compressing the canister 2 is stored in a resilient loading element in the form of a torsion spring 7. To load the torsion spring 7, the actuation mechanism 6 includes a loading mechanism consisting of a loading member in the form of a rotatable spindle 8 and two contact members in the form of buttons 9 which protrude from the housing as shown in FIG. 1. Depression of the buttons 9 towards one another, relative to the housing 1, drives the loading member 8 to load the torsion spring 7 through a cam arrangement between the buttons 9 and spindle 8.

The torsion spring 7 biases compression of the canister 2 by engaging a canister engagement member in the form of a lever 10 which depresses the body 3 of the canister towards the stem 4 held in the nozzle block 11.

To allow storage of the actuation force in the torsion spring 7 after loading, the actuation mechanism 6 includes a triggering mechanism. This includes a locking lever 12 which holds the canister engagement lever 10 against compression of the canister 2. To release the canister engagement lever 10, the triggering mechanism further includes a vane in the form of a flap 13 which in a rest state holds the locking lever 12 in place. Inhalation at the mouthpiece 5 moves the flap 13 to release the locking member 12. This in turn releases the canister engagement lever 10 allowing the torsion spring 7 to drive compression of the canister 2.

The actuation mechanism 6 further includes a locking mechanism which locks the spindle 8 after loading of the torsion spring 7, thereby holding the torsion spring 7 in its loaded state before triggering and locking the canister in its compressed state after triggering.

The locking mechanism includes a catch 14 which, in a locking position, catches the spindle 8 and holds the torsion spring 7 in its loaded state. The locking mechanism further includes an intermediate member 15. A resilient biassing element in the form of a spring 16 is provided between the catch 14 and the intermediate member 15 to bias the catch 14 towards its locking position. The spring 16 allows deflection of the catch 14 by the spindle 8 during loading of the torsion spring 7.

Prior to inhalation the intermediate member 15 is held in place by the canister engagement lever 10. Upon inhalation at the mouthpiece 5, the flap 13 engages the intermediate member 15 to hold it in place. After compression by the canister engagement lever 10, the canister 2 is locked in its compressed state by the catch 14 of the locking mechanism holding the spindle 8 in place.

When the level of inhalation at the mouthpiece falls below a predetermined threshold, the flap 13 releases the intermediate member 15 to unload the biassing element 16 which in turn allows the catch 14 to release the spindle 8. After release by the catch 14, the spindle 8, torsion spring 7 and canister engagement lever 10 move upwardly and the canister resets.

Figure 7:
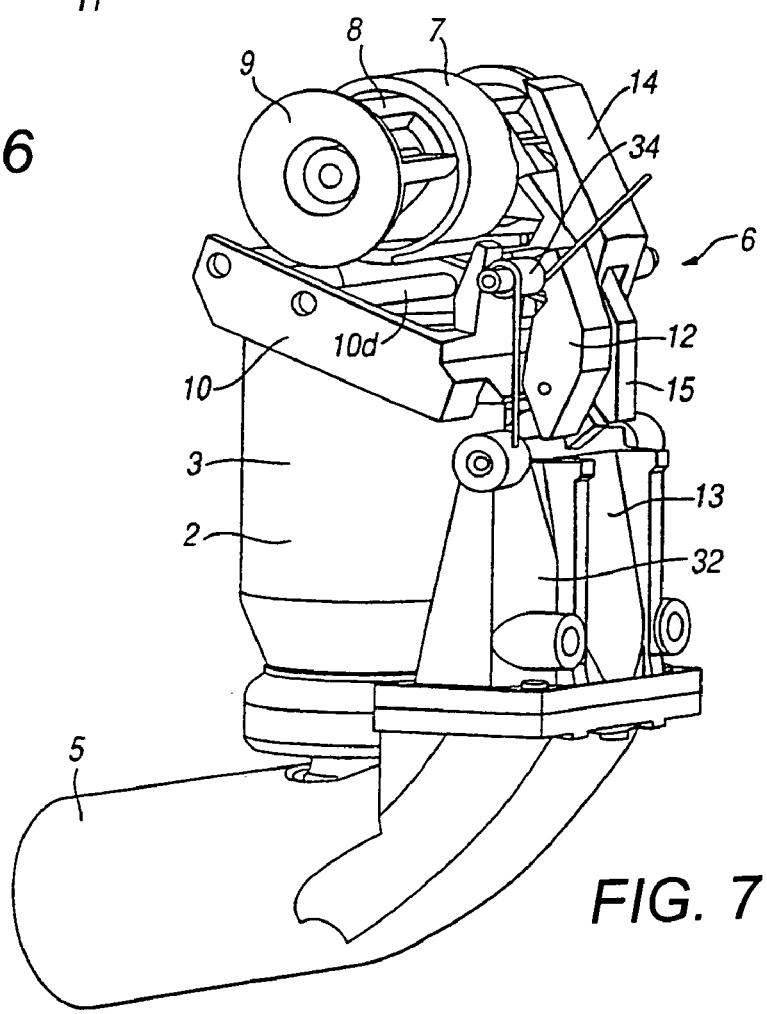
FIG. 7 is a view from the side and rear of the actuation mechanism.

Now there will be given a detailed description of the actuation mechanism 6, the entirety of which is illustrated in FIG. 7 and parts of which are illustrated in FIGS. 8 to 13.

Figure 8:
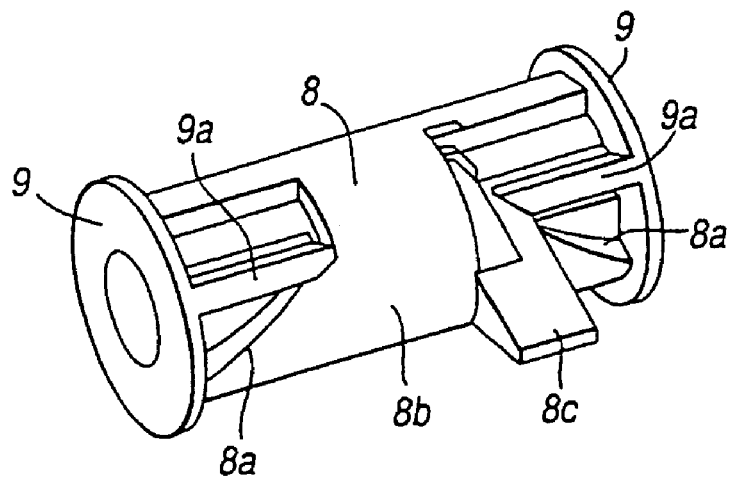
FIG. 8 is a view from the rear of the spindle.

The loading mechanism is illustrated in FIG. 8 and consists of a rotatable spindle 8 and two contact members in the forms of buttons 9 at both ends. The spindle 8 is rotatably mounted in the upper housing portion 19 about an axis orthogonal to the axis of the cylindrical body 3 of the canister 2. The spindle 8 has a pair of cam surfaces 8a disposed on opposite sides of the rotational axis of the spindle 8. The buttons 9 are mounted in the housing to be movable in a movement direction parallel to the rotational axis of the spindle 8. The buttons 9 each have a pair of inwardly projecting cam followers 9a which each engage a respective cam surface 8a of the spindle 8. The cam arrangement of the cam surfaces 8a and the cam followers 9a between the spindle 8 and the buttons 9 causes depression of the buttons 9 to drive rotation of the spindle 8.

Figure 9:
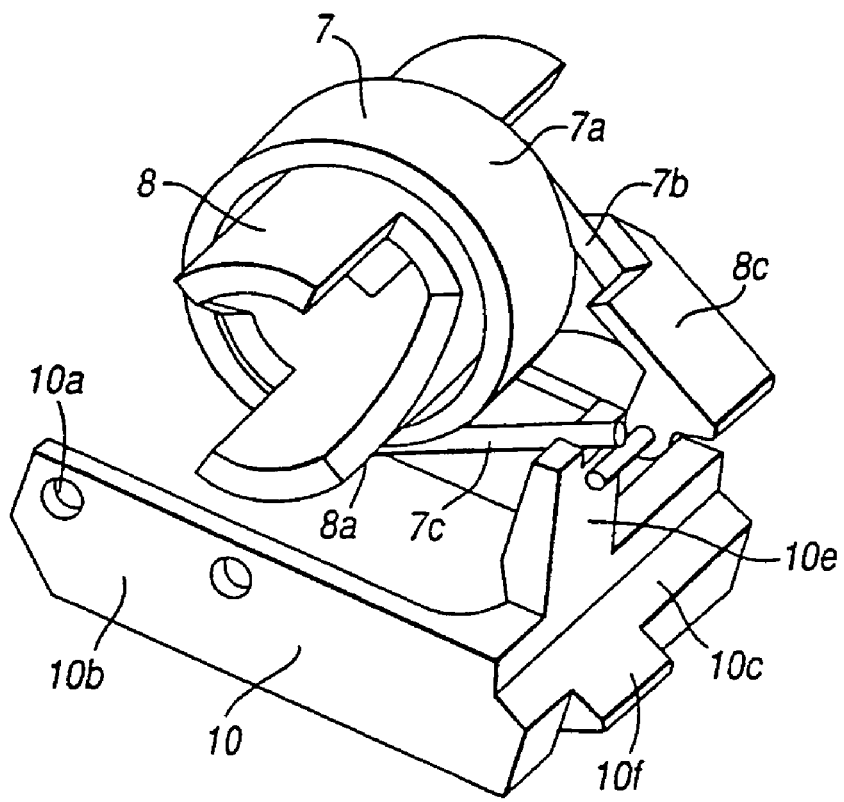
FIG. 9 is a view from the side, rear and above showing the arrangement of the resilient loading element.

As illustrated in FIG. 9, the torsion spring 7 which forms the resilient loading element is disposed with its coils 7a encircling a central cylindrical surface 8b of the spindle 8. A catch arm 8c protrudes radially from the spindle 8. A first leg 7b of the torsion spring 7 is restrained by the catch arm 8c so that the movement of the spindle 8 driven by the buttons 9 loads the torsion spring 7.

Figure 10:
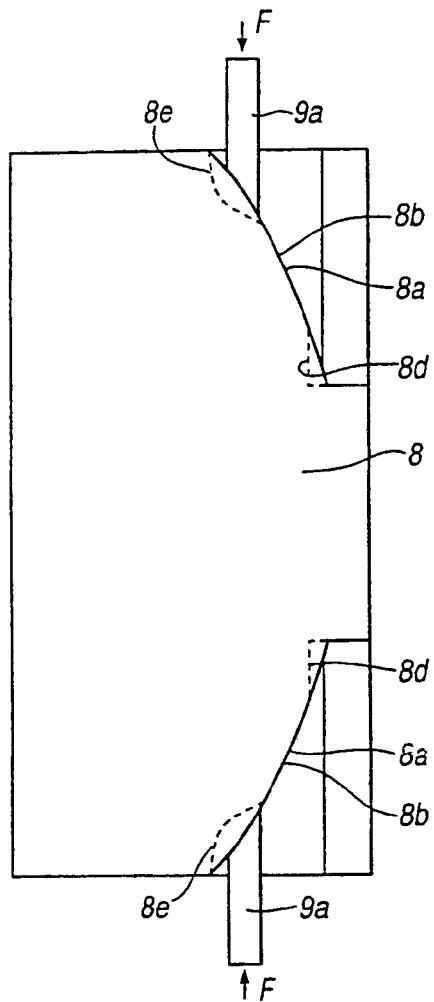
FIG. 10 is a schematic view of the cam surfaces formed on the spindle.

As illustrated schematically in FIG. 10, the cam surfaces 8a have a non-linear shape which causes the gearing ratio of the amount of driven movement of the spindle 8 to the amount of movement of the buttons 9 to be a non-linear function of the rotational position of the spindle 8. The major portion 8b of each cam surface 8a is shaped with increasing pitch to compensate for the increased reactive loading force applied by the torsion spring 7 to the spindle 8 as the buttons 9 are depressed. In particular, they are shaped such that the necessary force applied to the buttons is substantially constant so the user feels a linear resistance. As the torsion spring 7 has a linear spring constant, this is achieved by shaping the major portion 8b of each cam surface 8a such that the gearing ratio is inversely proportion to the rotational position of the spindle 8.

Optionally, the outermost portion of the cam surfaces 8a which are contacted by the cam followers 9a during the initial portion of the driven movement of the spindle may have a decreased pitch, for example as illustrated by the dotted lines 8e. This is to reduce the gearing ratio relative to the subsequent major portion 8b. In this way the user initially feels a low resistance to movement of the buttons 9. This improves the feel perceived by the user and also assists the user in applying force.

Another option is to provide the final portion of the cam surface 8a with a detent, for example as illustrated by the dotted lines 8d. When the end of the cam followers 9a reach the detent 8d, the cam surface 8a of the spindle 8 no longer exerts a force urging the buttons outwardly on the buttons 9. At this position the detent 8d is urged by the torsion spring 7 against the side of the cam followers 9a and therefore holds the buttons 9 in their innermost position. This prevents the buttons 9 from loosely sliding back and forth after the torsion spring 7 has been loaded.

As shown in FIG. 9, the torsion spring 7 engages a canister engagement lever 10 which is pivotally mounted to the interior of the housing about an axis 10a. The canister engagement lever 10 is generally U-shaped with two parallel sides 10b connected by a cross piece 10c. A bar 10d extending between the two sides 10b bears on the body 5 of the canister 2. A mount 10e formed on the cross-piece 10c is engaged by the second leg 7c of the torsion spring 7, whereby loading of the torsion spring 7 biasses the lever 10 to compress the canister 2. The canister engagement lever 10 is biased upwardly by a reset spring (not shown), which may be arranged as a torsion spring on the axis 10a, but this is weaker than the torsion spring 7.

The torsion spring 7, spindle 8 and canister engagement lever 10 are all rotatable about axis orthogonal to the cylindrical axis of the body 5 of the canister 2. This provides a simple and reliable loading mechanism particularly because of the arrangement of the torsion spring 7 with its coils 7a encircling the spindle 8. Some or all of these elements could alternatively be linearly movable in a plane parallel to the cylindrical axis of the body 5 of the canister 2 to achieve a loading mechanism which is equally simple to construct. However rotatable elements are preferred from the point of view of reliability in repeated use of the actuation mechanism 6.

On the other hand, the movement of the buttons in a direction orthogonal to the cylinder axis of the body 3 of the canister 2 assists the user in application of force to the loading mechanism. As typical for inhalers, the housing 1 extends in the direction of the cylindrical axis of the body 3 of the canister 2, so may be easily held in the palm of a hand with the buttons 9 protruding from either side. Thus the buttons 9 are easily depressed between a finger and thumb. Alternatively a single button could be provided allowing loading in a similar manner by the user pressing the button and the housing on the opposite side to the button. Either configuration also allows loading by laying the inhaler on a surface and applying force for example with the palm of a hand. This facilitates loading by a user with limited finger control or movement, for example a chronic arthritis sufferer.

Figure 11:
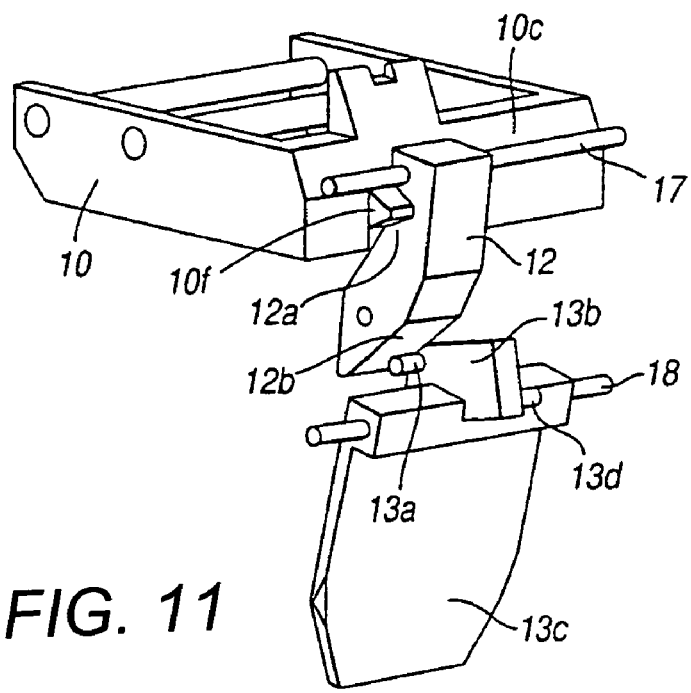
FIG. 11 is a view from the side and rear of the triggering mechanism.
Figure 12:
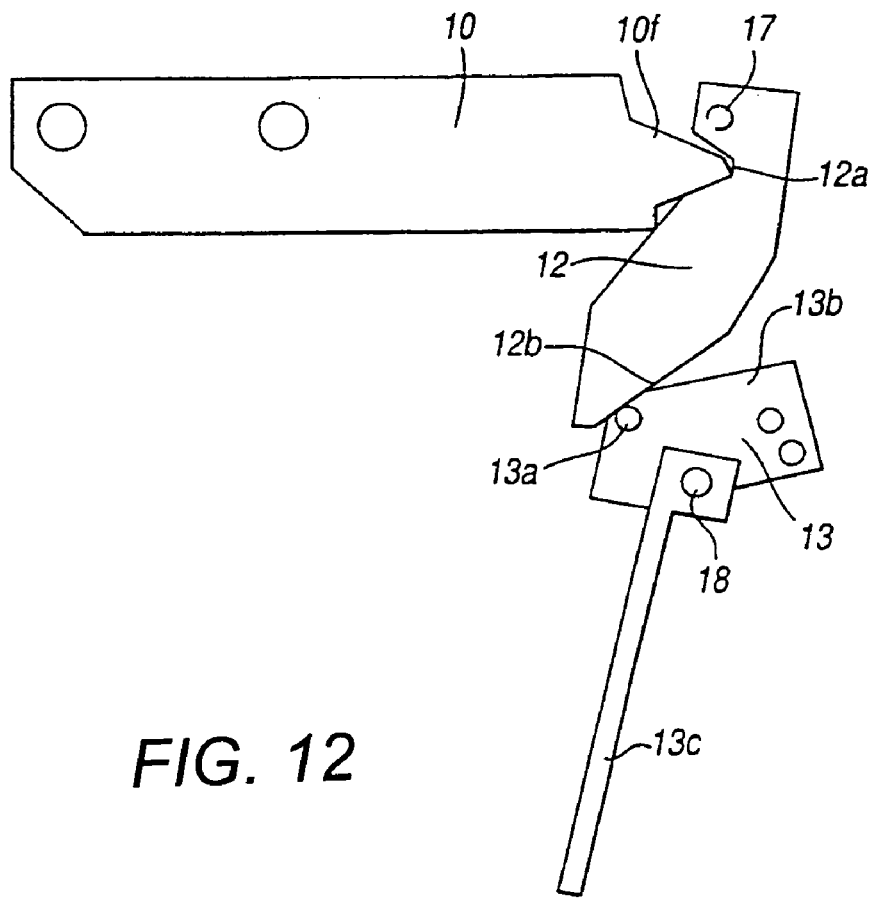
FIG. 12 is a side view of the triggering mechanism.

The actuation member mechanism 6 includes a triggering mechanism as illustrated in FIGS. 11 and 12 which allows storage of the actuation force in the torsion spring 7 after loading.

The triggering mechanism includes a locking lever 12 which is pivotably mounted on an axle 17 extending across the interior of the housing 1. The locking lever 12 has a notch 12a adjacent the axle 17. In a reset state shown in FIG. 12, the notch 12a holds a protrusion 10f protruding from the cross-piece 10c of the canister engagement lever 10, thereby holding the lever 10 against compression of the canister 2. The locking lever 12 is weakly biased towards the position shown in FIGS. 11 and 12 by a reset spring 34 arranged as a torsion spring on the axle 17.

The triggering mechanism further includes a vane in the form of a flap 13 which is rotatably mounted on an axle 18 extending across the interior of the housing 1. The flap 13 biased by a reset spring (not shown), which may be arranged as a torsion spring on the axle 18, towards the position shown in FIG. 12. The flap 13 has a locking lever engagement surface 13a which protrudes from a block 13b positioned above the axle 18. In the position shown in FIG. 12, the engagement surface 13a engages a contact surface 12b formed on the end of the locking lever 12 distal from the axle 17 to hold the locking lever 12 in place holding the canister engagement lever 10.

The flap 13 is disposed in the composite duct formed by the duct 24 and the flap duct 32 extending from the mouthpiece 5 with a flap portion 13c extending across the composite duct at the opposite end from the mouthpiece 5, where the duct opens into the interior of the housing 1. Therefore, the flap 13 is responsive to inhalation at the mouthpiece 5.

Inhalation of the mouthpiece draws the flap portion 13c into the flap duct 32 (clockwise in FIG. 2 and anticlockwise in FIG. 12). Such rotation of the flap 13 allows the locking lever engagement surface 13a to move out of contact with the contact surface 12b of the locking lever 12.

The upper housing portion 19 also mounts a button 35 disposed adjacent the flap 13 above the axle 18 so that depression of the button 35 rotates the flap 13 in the same direction as inhalation at the mouthpiece 5. Therefore, the button 35 allows the actuation mechanism 6 to be manually released without inhalation at the mouthpiece 5, for example to allow actuation of the canister 2 for testing.

When the canister engagement lever 10 is loaded by the torsion spring 7, release of the locking lever 12 by the flap 13 allows the canister engagement lever 10 to be driven to compress the canister 2. The protrusion 10f deflects the locking lever 12 (anticlockwise in FIG. 12) as the canister engagement lever 10 passes.

Figure 13:
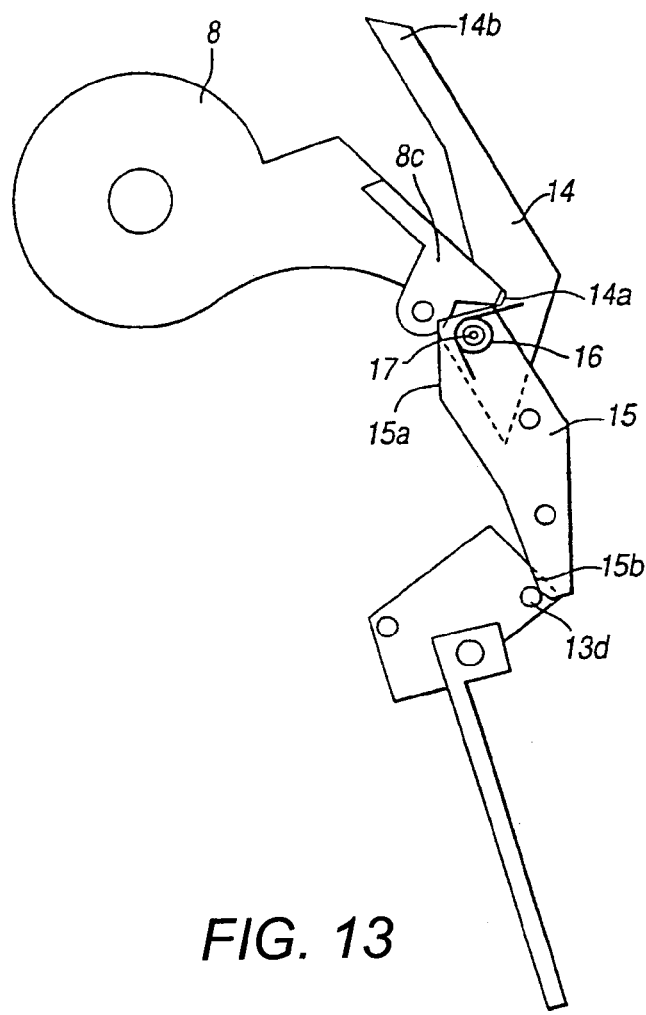
FIG. 13 is a side view of the locking mechanism.

As illustrated in FIG. 13, the actuation mechanism 6 further includes a locking mechanism for locking the spindle 8 after loading of the torsion spring 7. The locking mechanism comprises a catch 14 and an intermediate member 15 which are both pivotally mounted on the axle 17, adjacent the locking lever 12. Before compression of the canister 2, the intermediate member 15 is held in the position illustrated in FIG. 13 by the cross-piece 10c of the canister engagement lever 10 contacting a first contact surface 15a adjacent the axle 17. A resilient biasing element in the form of a torsion spring 16 is connected between the catch 14 and the intermediate member 15 and loaded to bias the catch 14 towards its locking position shown in FIG. 13.

The catch 14 has a notch 14a adjacent the axle 17 for engaging the arm 8c of the spindle 8 after rotation to the position illustrated in FIG. 13 where the torsion spring 7 is loaded. In this position, the loading provided by the spring 16 prevents release of the spindle 8 and thereby holds the torsion spring 7 in its loaded state. Before loading, the arm 8c of the spindle 8 is positioned above the end 14b of the catch 14 distal from the axle 17. When the spindle 8 is driven downwards by depression of the buttons 9, the arm 8c of the spindle engages the end 14b of the catch 14 and deflects the catch 14 by compressing the spring 16 to allow passage of the arm 8c of the spindle 8.

The flap 13 further includes a stud 13d protruding from the block 13b on the opposite side of the axle 18 from the locking lever engagement surface 13a. Upon inhalation at the mouthpiece 5, the flap 13 moves to the position illustrated in FIG. 13 where the stud 13d engages a second contact surface 15b of the intermediate member 15 distal from the axle 17. Prior to this point, the stud 13d does not contact the second contact surface 15b but the intermediate member 15 has been held in place by the canister engagement lever 10. Movement of the flap 13 triggers the triggering mechanism to release the canister engagement member 10 which moves downwards out of contact with the intermediate member 15. However, the stud 13d catches the contact surface 15b and so continues to hold the intermediate member 15 with the spring 16 loaded. Accordingly, the catch 14 remains in its locking position locking the spindle 8 by engagement of the arm 8c of the spindle 8 in the notch 14a of the catch 14.

Subsequently, when the level of inhalation of the mouthpiece falls below a predetermined threshold, the flap moves out of contact with the intermediate member 15 (clockwise in FIG. 13). The level of the predetermined threshold at which the flap 13 releases the intermediate member 15 is controlled by the shape of the second contact surface 15b of the intermediate member 15.

After release by the flap 13, the intermediate member 15 is driven by spring 16 which unloads (clockwise in FIG. 13). Such unloading of the spring 16 reduces the force by which the catch 14 is biassed towards its locking position. Accordingly, the force of the torsion spring 7 acting on the canister engagement lever 10 is sufficient to force the catch arm 8c of the spindle 8 out of the notch 14a. Accordingly, the spindle 8, the torsion spring 7 and canister engagement lever 10 are able to move upwardly biased by the reset spring acting on the canister engagement lever 10, thereby allowing the canister to reset.

Figure 14A:
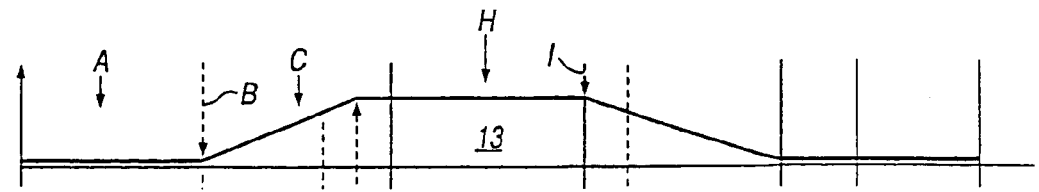
FIG. 14A to 14F are graphs showing the angular positions of the elements of the actuation mechanism during its operation sequence.
Figure 14B:
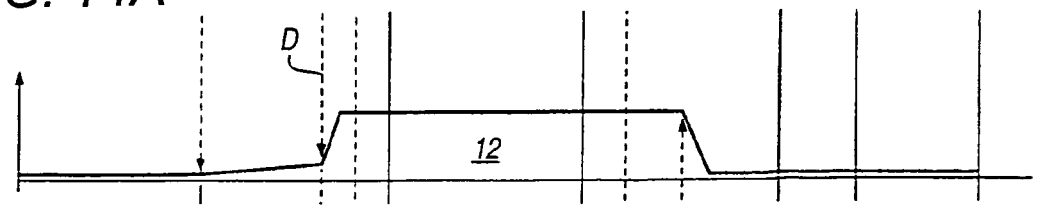
Figure 14C:
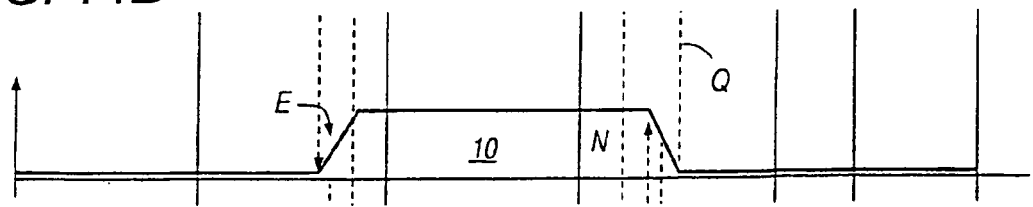
Figure 14D:
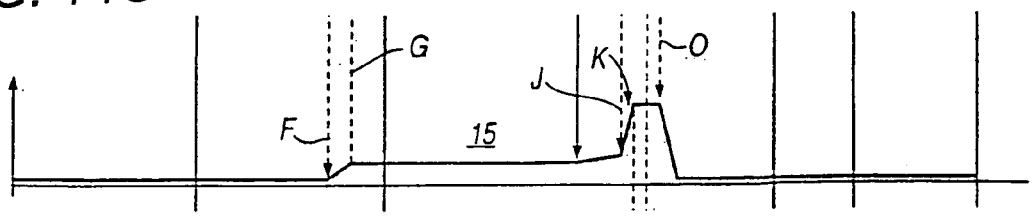
Figure 14E:
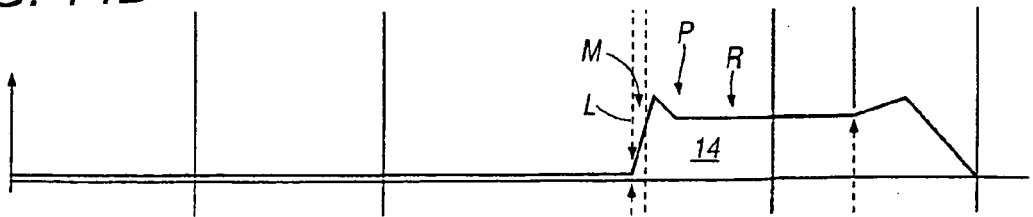
Figure 14F:

The sequence of operation of the actuation mechanism 6 will now be described with reference to FIGS. 14 to 22. FIG. 14A to 14F are graphs showing the angular positions of the various elements of the actuation mechanism 6. In particular, FIG. 14A illustrates the angular position of the flap 13; FIG. 14B illustrates the angular position of the locking lever 12; FIG. 14C illustrates the angular position of the canister engagement lever 10; FIG. 14D illustrates the angular position of the intermediate member 15; FIG. 14E illustrates the angular position of the catch 14; and FIG. 14F illustrates the angular position of the spindle 8. Various states and positions of the actuation mechanism 6 are labelled by the letters A to R in FIGS. 14 and FIGS. 15 to 22 illustrate the actuation mechanism 6 in some of these states with the views from opposite sides being suffixed by the letters A and B, respectively.

Figure 15A:
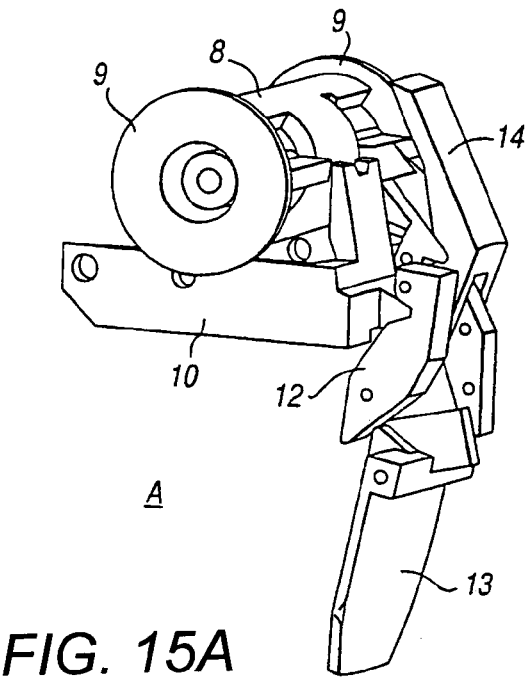
FIGS. 15 to 22 are views of the actuation mechanism in various states during its operation sequence with views from opposite sides being suffixed by the letters A, B respectively.
Figure 15B:
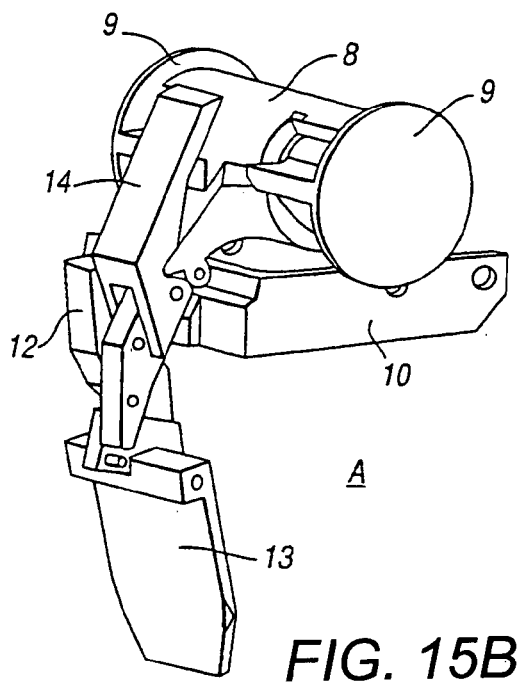
Figure 16A:
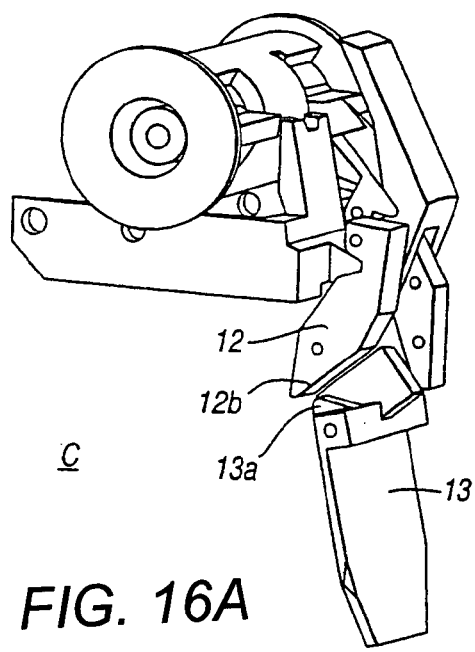
Figure 16B:
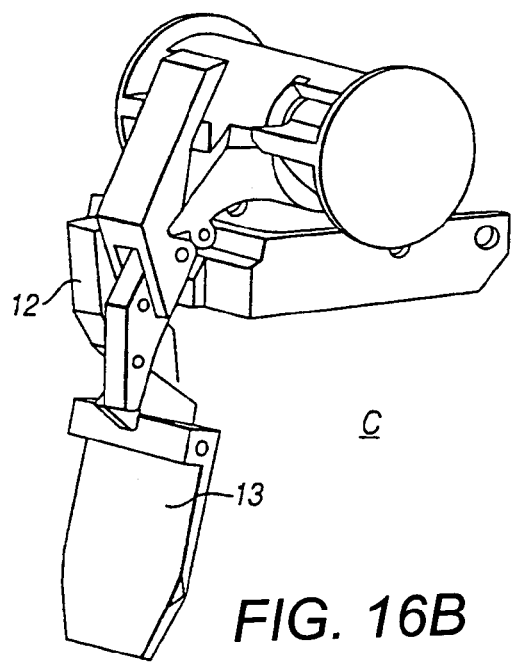
Figure 17A:
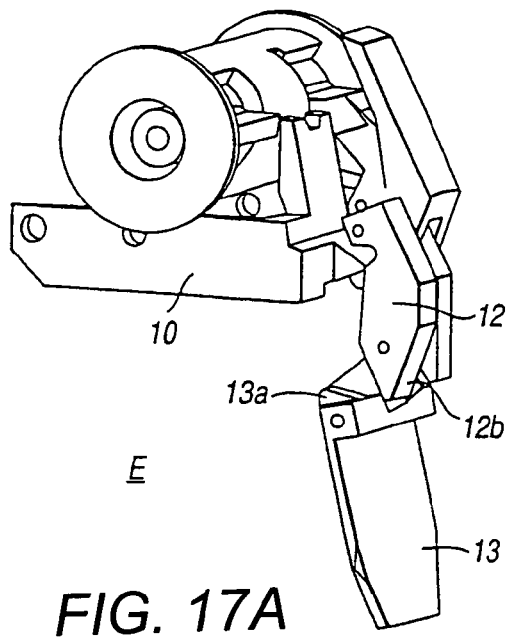
Figure 17B:
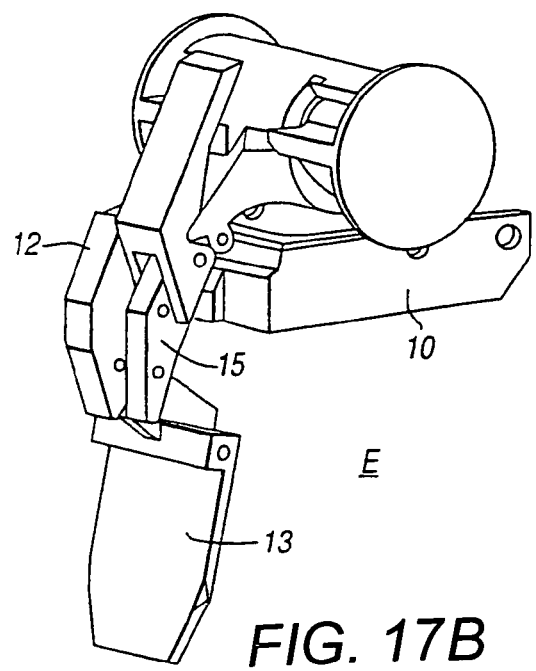
Figure 18A:
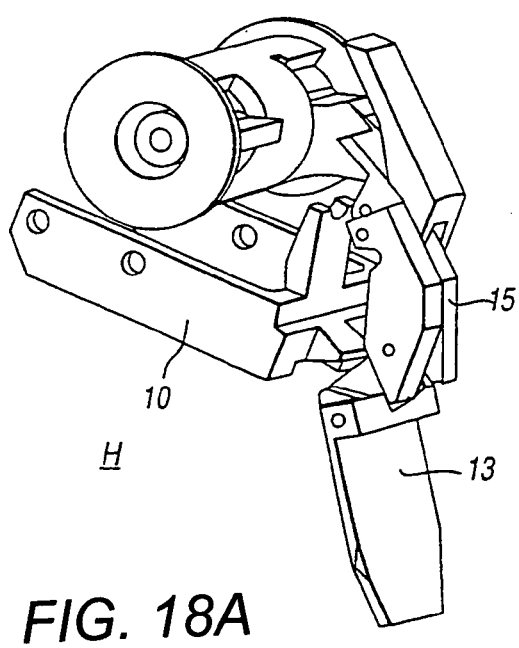
Figure 18B:
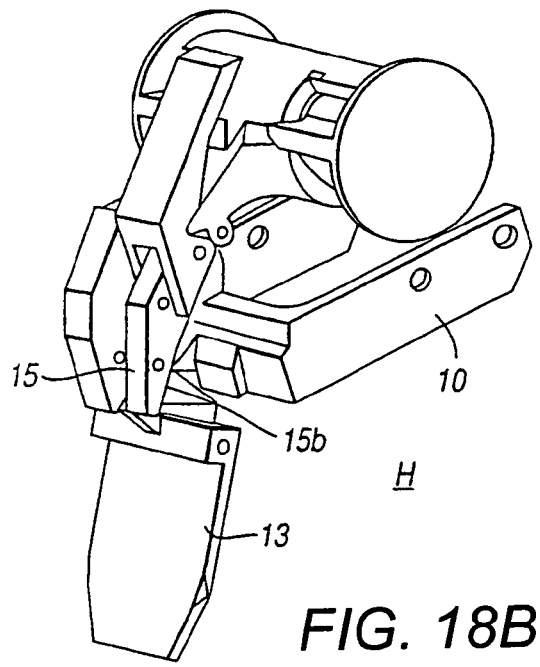
Figure 19A:
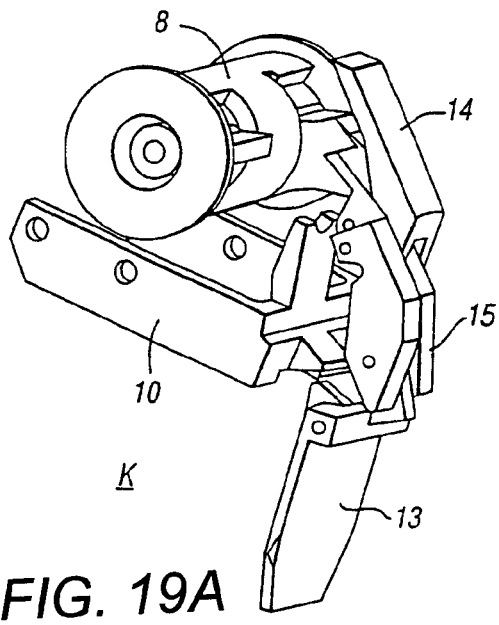
Figure 19B:
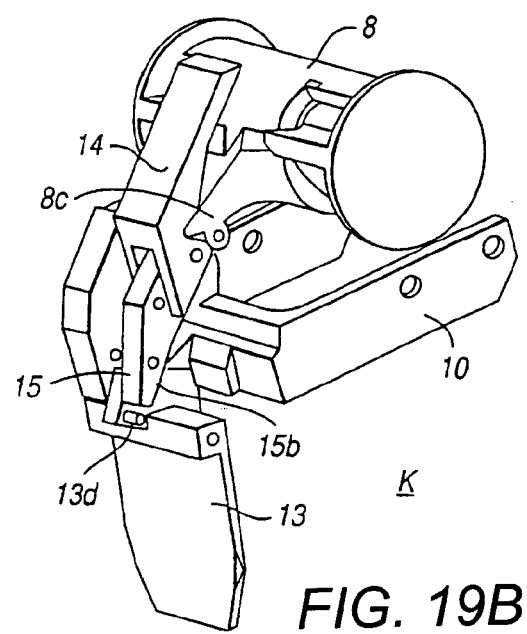
Figure 20A:
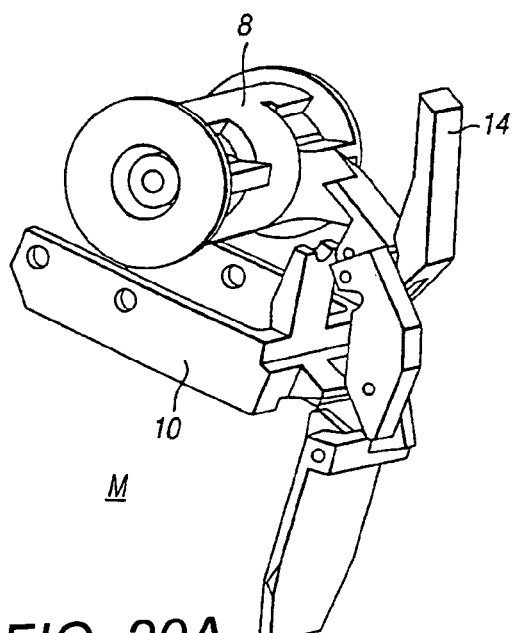
Figure 20B:
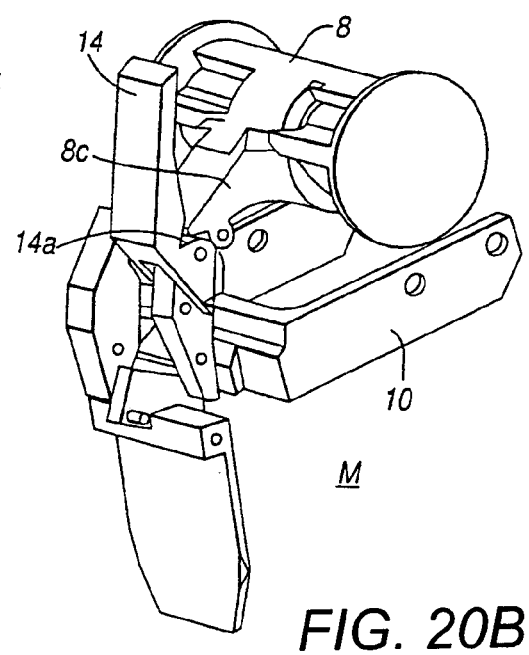
Figure 21A:
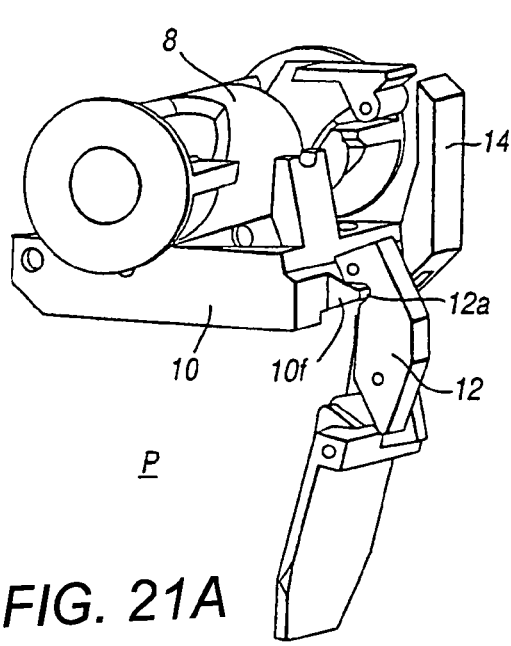
Figure 21B:
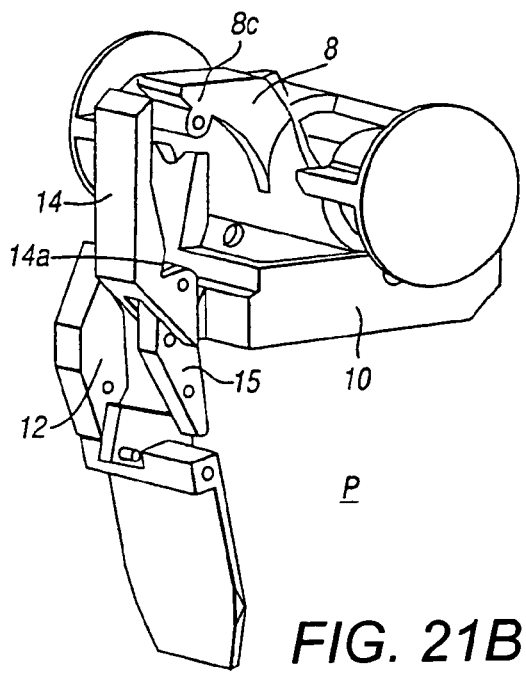
Figure 22A:
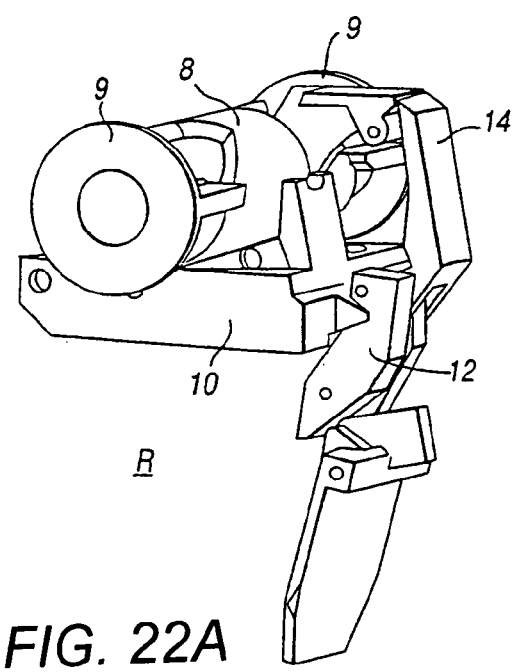
Figure 22B:
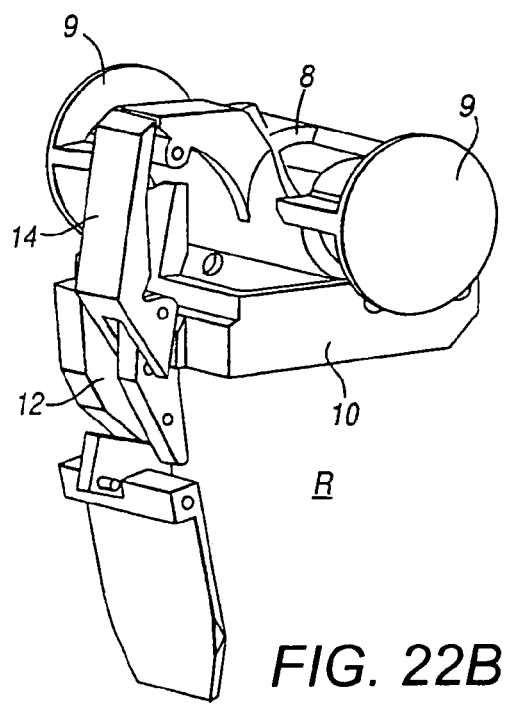

The sequence commences in state A as shown in FIGS. 15A and 15B, in which the torsion spring 7 has been loaded by depression of the buttons 9 and the spindle 8 is locked by the catch 14. In state A, the canister engagement lever 10 is held by the locking lever 12. The inhaler may be stored with the actuation mechanism 6 in state A.

At position B, the user starts to inhale. The flap 13, being responsive to such inhalation, starts to move. The shape of the contact surface 12b allows the locking lever 12 to start moving slowly. The actuation mechanism 6 is now in state C illustrated in FIGS. 16A and 16B.

At position D, the locking lever engagement surface 13a of the flap 13 releases the contact surface 12b of the locking lever 12. Accordingly, the canister engagement member 10 under the loading of the torsion spring 7 starts to rotate downwards, deflecting the locking lever 12 against its reset spring as the projection 10f moves out of the notch 12a. The actuation mechanism is now in state E illustrated in FIGS. 17A and 17B.

At position F, the canister engagement lever 10 moves out of contact with the first contact surface 15a at the intermediate member 15 which therefore strates to move under the biasing force of spring 16. However, the intermediate member 15 only moves a short way because at position G it is caught by the flap 13, in particular by the bar 13d of the flap 13 contacting the second contact surface 15b. This contact stops the movement of the flap 13 and the intermediate member 15.

The movement of the canister engagement lever 10 compresses the body 3 of the canister 2 relative to the stem 4 held in the nozzle block 11, thereby causing the canister 2 to deliver a dose of medicament. The nozzle block 11 directs the dose of medicament out of the mouthpiece at which the user is inhaling. The actuation mechanism 6 is now in state H illustrated in FIGS. 18A and 18B.

When the level of inhalation starts to fall, at position I the flap 13 under the biasing force of its reset spring starts to move back, closing the duct. This movement of the flap 13 causes the intermediate member 15 to move slightly due to the shape of the second contact surface 15B.

When the level of inhalation falls below the predetermined threshold, at position J the bar 13d of the flap 13 moves out of contact with the second contact surface 15b. This releases the intermediate member 15. Under the action of the spring 16, the intermediate member 15 moves to unload the spring 16. The actuation mechanism 6 is now in state K illustrated in FIGS. 19A and 19B.

At position L the load on the catch 14 from the spring 16 reduces to the extent that the catch 15 can no longer hold the spindle 8. The force of the torsion spring 7 forces the arm 8c of the spindle 8 upwards and out of engagement with the notch 14a of the catch 14. This forces the catch 14 backwards. The actuation mechanism 6 is now in state M illustrated in FIGS. 20A and 20B.

At position N, the torsion spring 7 reaches its neutral, unloaded position, so there is no load between the canister engagement lever 10 and the spindle 8. Thereafter the canister engagement lever 10 and the torsion spring 8 are moved under the action of the reset spring biasing the canister engagement lever 10.

At position O, the canister engagement lever 10 contacts the first contact surface 15a of the intermediate member 15 and forces it backwards. The actuation mechanism is now in state P illustrated in FIGS. 21A and 21B. This loads the spring 16 and pushes the catch 14 towards its locking position until the catch 14 contacts the arm 8c of the spindle 8 which has now passed out of the notch 14a.

At position Q, the projection 10f of the canister engagement lever 10 moves into the notch 12a of the locking lever 12 which snaps back into its locking position under the action of its reset spring. The actuation mechanism 6 is now in state R illustrated in FIGS. 22A and 22B. In state R, the canister is reset and ready to be compressed again for delivery of the next dose, but the actuation mechanism 6 is relaxed with the torsion spring 7 unloaded. The rotation of the spindle 8 has forced the buttons 9 outwards to the position illustrated in FIGS. 22A and 22B. The actuation mechanism 6 is ready to be loaded once again by compression of the buttons 9. The user is instructed to do this immediately after inhalation, so that the canister may be stored in a state ready to be used simply by inhaling at the mouthpiece 5.

When the user depresses the buttons 9 at position S, this drives the spindle 8 downwards. The arm 8c of the spindle 8 deflects the catch 14 slightly against the loaded spring 16 until the arm 8c moves into the notch 14a. This allows the spring 16 to snap the catch 14 into its locking position.

Figure 23:
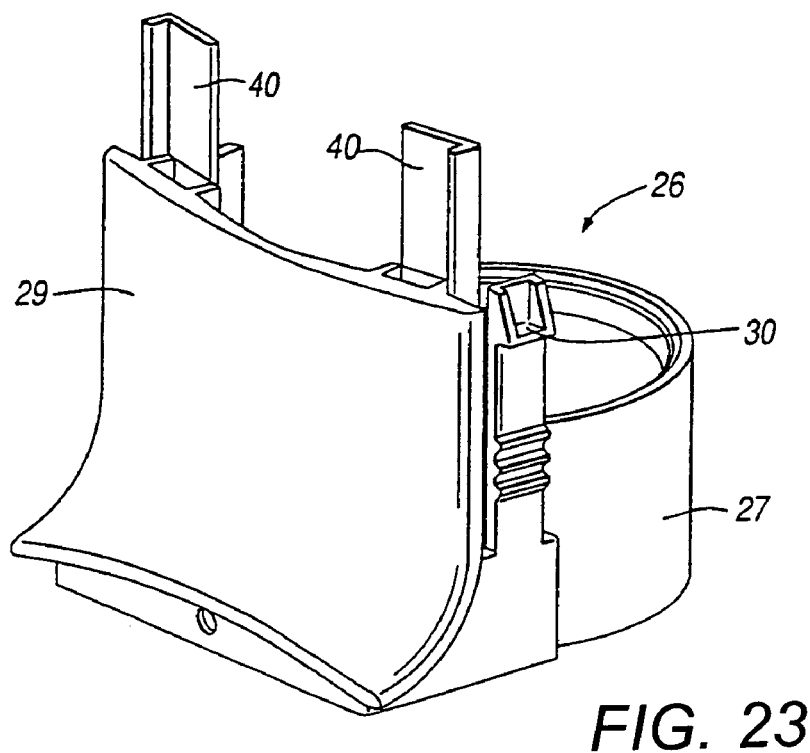
FIG. 23 is a view of the collar on the front and side.

As shown in FIG. 23, the collar 26 is provided with posts 40 extending above the front panel 29 parallel to the axis of the body 3 of the canister 2 to guide fitting of the collar 26 to the upper housing portion 19. The posts 40 are set back from the front panel 29 to define a channel therebetween. The collar 26 serves as a mount for an indication member 41 slidably mounted in one of the channels, as illustrated in the views of FIGS. 24 and 25, in which the front panel 29 is cut-away, the indication member 41 being illustrated in detail in FIG. 26.

Figure 24:
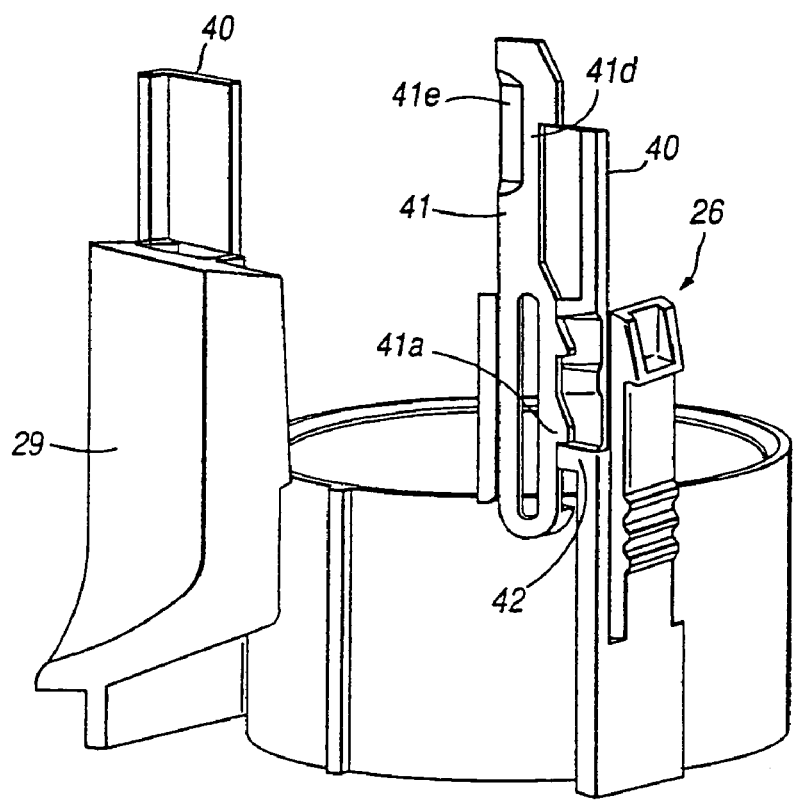
FIGS. 24 and 25 are views of the collar from the front and side with the indication member in its second and first states, respectively, and with the front panel cut away to illustrate the mounting of the indication member.
Figure 25:
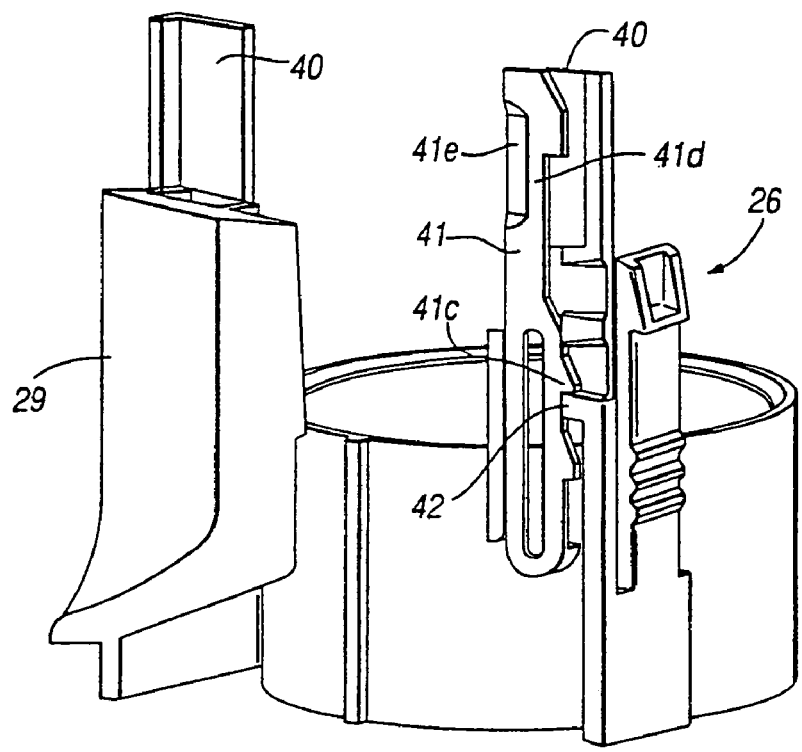
Figure 26:
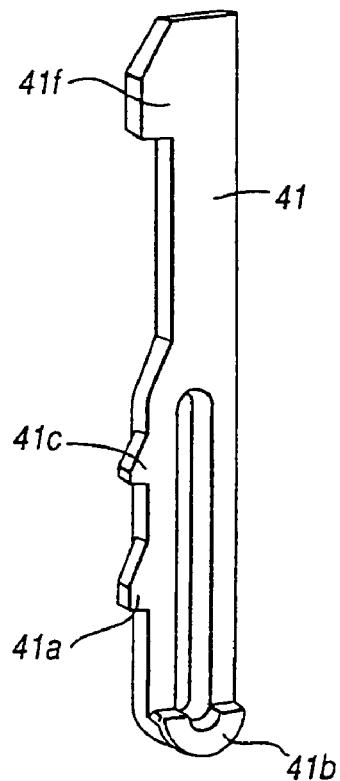
FIG. 26 is a view from the rear of the indication member.

The indication member 41 is movable from a first state illustrated in FIG. 25 to a second state illustrated in FIG. 24. A ratchet mechanism in the form of a ratchet tooth 41a formed on the side of the indication member 41 and a pawl 42 protruding from the collar 26 is provided to allow movement only in the direction from the first to second state, so this movement is irreversible.

Indication member 41 has a protrusion 41b at its lowermost end for engagement of the lower end of the post 40 and the indication member 41 is in its second state to retain the indication member 40 on the collar.

A second ratchet tooth 41c is provided above the first ratchet tooth 41a to hold the uppermost end 41d of the indication member 41 above the top edge of the front panel 29 of the collar 26. The uppermost end 41d of the indication member 41 is provided with a recess 41e facing towards the front panel 29 of the collar 26 and a sideways protrusion 41f which both interact with the inhaler as described below.

Figure 27:
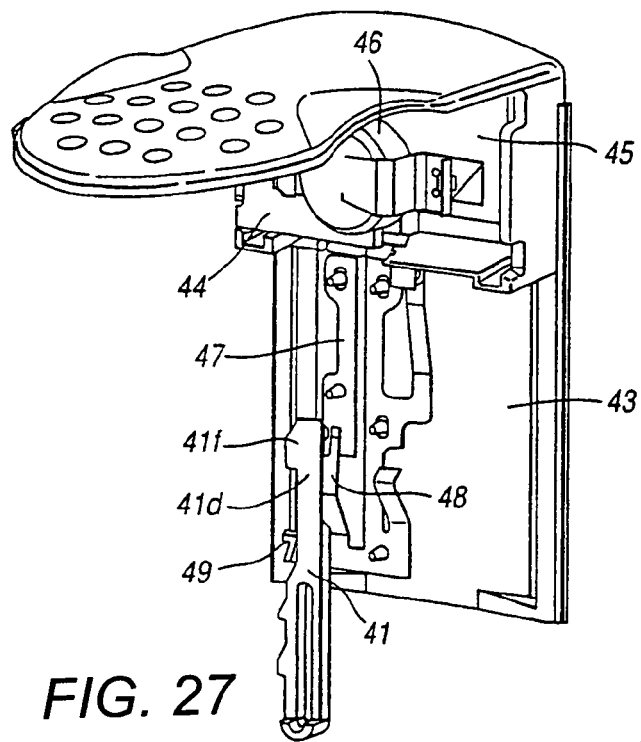
FIGS. 27 and 28 are views from the rear of the front panel of the upper housing portion showing the indication member in its two possible states.
Figure 28:
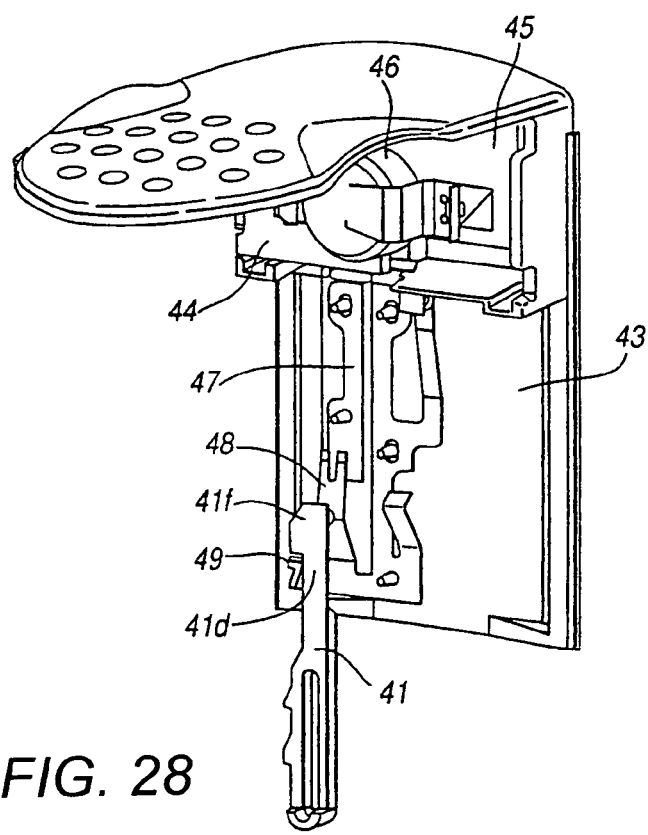

As illustrated in FIGS. 27 and 28, on the rear face of the front panel 43 of the upper housing portion 19 of the inhaler is mounted an electronic module 44. The electronic module 44 includes an LCD display 45 visible from the front face of the front panel 43, a battery 46 to power the electronic module 44 and a metallic strip 47 extending down the rear face of the front panel 43. The metallic strip 47 has a switch contact 48 which completes an electrical circuit around the metallic strip 47 when the contact 48 is closed. The resilience of the metallic strip 47 biases the switch contact 48 open.

The canister 2 is normally provided to the user with an indication member 41 mounted in the collar in its first state (as in FIG. 25). When the canister 2 and collar 26 are fitted into the inhaler, the indication member 41 in its first state has the position illustrated in FIG. 28 where its uppermost end 41d engages and closes the switch contact 48.

A catch 49 protrudes from the rear face of front panel 43 and is positioned to be below protrusion 41f after fitting of the canister 2 and collar 26 in the inhaler. The upper surface of the protrusion 41f on the indication member 41 and the lower surface of the catch 49 are sloping to allow relative deflection as they pass one another during fitting of the collar 26 to the upper housing member 19. At this time, the pawl 42 engages the second ratchet tooth 41c as shown in FIG. 25 to force the indication member 41 past the catch 49.

The electronic module 44 recognises closing of the switch contact 48 and controls the LCD display 45 in response thereto to display an indication of the fact that a canister 2 has been loaded and that the canister 2 is a fresh canister 2. For example a representation of a canister may be displayed.

On removal of the collar 26 and canister 2 from the upper housing portion 19, the catch 49 catches the protrusion 41f and holds the indication member 41 in place as the collar 26 is moved downwardly. This forces the pawl 42 over the first ratchet tooth 41a on the indication member 41, thereby moving the indication member 41 from its first state illustrated in FIG. 25 to its second state illustrated in FIG. 24. Subsequently, the projection 41b at the lowermost end of the indication member 41 engages the bottom of post 40 and prevents further retraction of the indication member 41 from the collar 26. This overcomes the catching by catch 49 and forces the protrusion 41f past the catch 49 and away from the upper housing portion 19. Consequently, a used canister 2 is left with the indication member 41 in its second state in the collar 26.

If a used canister 2 is fitted once again in the inhaler, with the indication member 41 is in its second state (as in FIG. 24), it takes the position relative to the front panel 43 of the inhaler shown in FIG. 27. In this case, on mounting of the collar 26 the pawl 42 engages the first ratchet tooth 41a. This forces the protrusion 41f from the position where the switch contact 48 is closed past the catch 49 to a position where the recess 41e is adjacent the switch contact 48 so the contact 48 protrudes into the recess 41e and is not engaged and the circuit around the metallic strip 47 is open.

The electronic module 44 recognises that the switch 48 is open and controls the LCD display 45 in response thereto to display an indication of the fact that a fresh canister has not been inserted, for example by showing a representation of a canister with a cross over the top. Preferably, the LCD display 45 always displays such a representation and the electronic module 44 ignores the brief closure of the switch contact 48 to maintain the same display so there is no change on loading of a used canister 2. In an alternative embodiment, the LCD display 45 is normally off and the electronic module firstly recognises the brief closure of the switch contact 48 to turn on the LCD display 45, thereby indicating insertion of a canister 2 and secondly recognises subsequent opening of the switch contact 48 to show a representation of the fact that the loaded canister is not fresh. In either case, the user is informed that the loaded canister 2 has been used before.

Of course, the indication member 41 could be fixed relative to the collar 26, for example by being integrally formed, in which case the switch contact 48 could be used to detect loading of a canister 2, although not to detect whether the loaded canister 2 is fresh.

The invention claimed is:

1. An inhaler for holding a canister of medicament, in combination with the canister,
   the canister having a mount secured thereto mounting an indication member movable irreversibly from a first position to a second position;
   the inhaler having means for moving the indication member from the first position to the second position on removal of the canister from the inhaler and detection means for detecting the position of the indication member, the means for moving the indication member comprising a catch for catching the indication member as the mount is removed from the inhaler.

2. An inhaler according to claim 1, wherein a ratchet arrangement is provided between the mount and the indication member.

3. An inhaler according to claim 2, wherein the ratchet arrangement comprises at least one ratchet tooth on the indication member and a pawl on the mount.

4. An inhaler according to claim 1, wherein a ratchet arrangement is provided between the mount and the indication member and, wherein the ratchet arrangement is further arranged to force the indication member past the catch on mounting of the canister with the indication member in its first position.

5. An inhaler according to claim 1, wherein the indication member has a catching surface arranged to be caught by the catch.

6. An inhaler according to claim 5, wherein the catching surface is formed on a protrusion on the indication member.

7. An inhaler according to claim 6, wherein the protrusion has a sloping surface for relatively deflecting the catch and protrusion on mounting of the canister.

8. An inhaler according to claim 1, wherein the catch has a sloping surface for relatively deflecting the catch and indication member on mounting of the canister.

9. An inhaler according to claim 1, wherein the catch protrudes from the interior of the inhaler.

10. An inhaler according to claim 1, wherein the indication member is slidably mounted to the mount.

11. An inhaler according to claim 1, wherein the detection means comprises an electrical switch contact.

12. An inhaler according to claim 1, wherein the indication member is shaped to engage the detection means only when the canister is held by the inhaler with the indication member in its first position.

13. An inhaler according to claim 12, wherein the indication member has a recess positioned to be adjacent the detection means to avoid engaging the detection means when the canister is held by the inhaler with the indication member in its second position.

14. An inhaler according to claim 1, wherein the inhaler further comprises display means for displaying an indication of the position of the indication member when a canister is held by the inhaler.

15. An inhaler for holding a canister of medicament which has a mount secured thereto mounting an indication member movable irreversibly from a first position to a second position, the inhaler having means for moving the indication member from the first position to the second position on removal of the canister from the inhaler and detection means for detecting the position of the indication member, the means for moving the indication member comprising a catch for catching the indication member as the mount is removed from the inhaler.

16. An inhaler according to claim 15, wherein the catch has a sloping surface for relatively deflecting the catch and indication member on mounting of the canister.

17. An inhaler according to claim 15, wherein the catch protrudes from the interior of the inhaler.

18. An inhaler according to claim 15, wherein the detection means comprises an electrical switch contact.

19. An inhaler according to claim 15, wherein the inhaler further comprises display means for displaying an indication of the position of the indication member when a canister is held by the inhaler.

20. A canister having a mount secured thereto mounting an indication member movable irreversibly from a first position to a second position on removal of the canister from an inhaler, the indication member having a catching surface arranged to be caught by a catch provided on the inhaler for catching the indication member as the mount is removed from the inhaler.

21. A canister according to claim 20, wherein a ratchet arrangement is provided between the mount and the indication member.

22. A canister according to claim 21, wherein the ratchet arrangement comprises at least one ratchet tooth on the indication member and a pawl on the mount.

23. A canister according to claim 20, wherein the catching surface is formed on a protrusion on the indication member.

24. A canister according to claim 23, wherein the protrusion has a sloping surface for relatively deflecting the catch and protrusion on mounting of the canister.

25. A canister according to claim 20, wherein the indication member is slidably mounted to the mount.

26. A canister according to claim 20, wherein the indication member is shaped to engage a detection means only when the canister is held by the inhaler with the indication member in its first position.

27. A canister according to claim 26, wherein the indication member has a recess positioned to be adjacent the detection means to avoid engaging the detection means when the canister is held by the inhaler with the indication member in its second position.

* * * * *